United States Patent
Kropfeld

(10) Patent No.: US 7,339,587 B2
(45) Date of Patent: Mar. 4, 2008

(54) METHOD FOR MEDICAL IMAGING AND IMAGE PROCESSING, COMPUTED TOMOGRAPHY MACHINE, WORKSTATION AND COMPUTER PROGRAM PRODUCT

(75) Inventor: Helmut Kropfeld, Forchhelm (DE)

(73) Assignee: Siemens Aktiengesellschaft, Munich (DE)

( * ) Notice: Subject to any disclaimer, the term of this patent is extended or adjusted under 35 U.S.C. 154(b) by 315 days.

(21) Appl. No.: 11/124,108

(22) Filed: May 9, 2005

(65) Prior Publication Data

US 2005/0249393 A1    Nov. 10, 2005

(30) Foreign Application Priority Data

May 10, 2004   (DE) ............... 10 2004 022 902

(51) Int. Cl.
*G06T 17/00* (2006.01)
(52) U.S. Cl. ............... 345/424; 345/419; 345/427; 345/473; 382/131
(58) Field of Classification Search ............... 345/419, 345/424, 427, 473; 382/131
See application file for complete search history.

(56) References Cited

U.S. PATENT DOCUMENTS

| | | | |
|---|---|---|---|
| 5,544,283 | A | 8/1996 | Kaufman et al. |
| 5,553,618 | A | 9/1996 | Suzuki et al. |
| 2003/0007593 | A1 | 1/2003 | Heuscher et al. |
| 2003/0233039 | A1 | 12/2003 | Shao et al. |

FOREIGN PATENT DOCUMENTS

DE    101 37 170 A1    2/2003

OTHER PUBLICATIONS

M. Tory et al., "4D Space-Time Techniques: A Medical Imaging Case Study," Proc. Visualization 2001 Conf., ACM Press, 2001, pp. 473-476.*
Marc Levoy, Efficient ray tracing of volume data, ACM Transactions on Graphics (TOG), v.9 n.3 p. 245-261, Jul. 1990.*
Willi A. Kalender. "Computertomographie", Gundlagen, Gerätetechnologie, Bildqualität, Anwendungen, Publicis MCD Verlag, Seiten 146-157.
German Search Report.
German Translation Aid.

* cited by examiner

*Primary Examiner*—Kimbinh T. Nguyen
(74) *Attorney, Agent, or Firm*—Harness, Dickey & Pierce

(57) ABSTRACT

A method is for medical imaging and image processing in the form of a perspective volumetric display. The method includes providing a multiplicity of temporally graded 3D data volumes at a multiplicity of instants, a 3D data volume, respectively being assigned to an instant; and prescribing a spatially absolutely fixed viewer position within an evaluation volume for at least one 3D data volume at a first instant. The method further includes determining a temporal correlation between the spatially absolutely fixed viewer position and the evaluation volume for at least one further 3D data volume at at least one second instant; determining a viewer position, spatially relatively fixed in relation to the evaluation volume, within the evaluation volume for the at least one further 3D data volume at the at least one second instant; and displaying the interior of the evaluation volume from a perspective of the spatially relatively fixed viewer position for the at least one further 3D data volume at the at least one second instant.

25 Claims, 2 Drawing Sheets

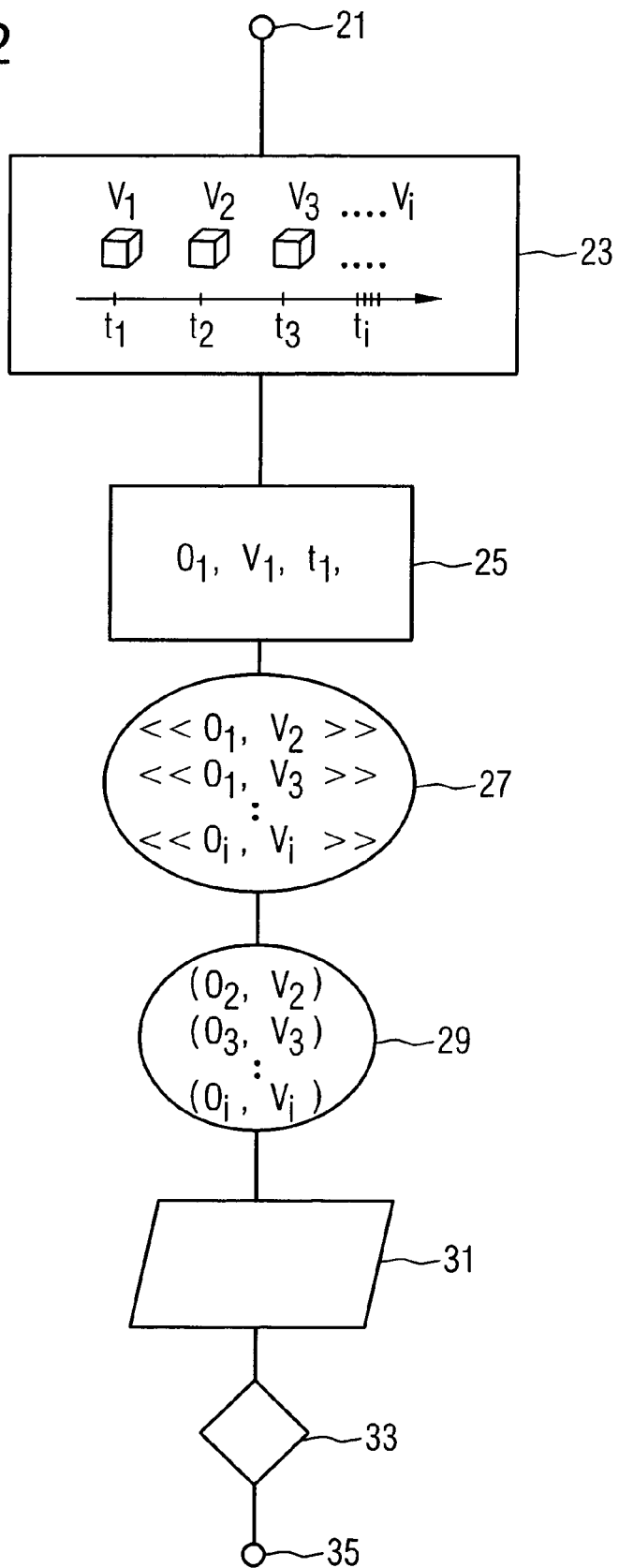

METHOD FOR MEDICAL IMAGING AND IMAGE PROCESSING, COMPUTED TOMOGRAPHY MACHINE, WORKSTATION AND COMPUTER PROGRAM PRODUCT

The present application hereby claims priority under 35 U.S.C. §119 on German patent application number DE 10 2004 022 902.3, filed May 10, 2004, the entire contents of which is hereby incorporated herein by reference.

FIELD OF THE INVENTION

The invention generally relates to a method for medical imaging and/or image processing; in one example in the form of a perspective volumetric display. The invention further generally relates to a computed tomography machine, a workstation and/or a computer program product.

BACKGROUND

Modern medical imaging methods generally supply images in digital form. The first step for this purpose within the scope of so called primary applications is to acquire data and provide the digital data in the course of a data reconstruction.

Computed tomograms, in particular, are present in digital form and can thus be further processed directly in a computer or a workstation. By applying so called secondary applications to the original images, it is possible to obtain images in a new orientation with two- or three-dimensional display (2D display, 3D display) in order to make a suitable overview available to the examiner. Such displays are intended, in particular, to form the basis of a subsequent diagnosis in the context of monitor findings.

Advantages of computed tomography may result, in particular, from the fact that there are no superposition problems as in the case of conventional radiography. Further, computed tomography offers the advantage of undistorted display independently of different magnification factors associated with the acquisition geometry.

In the meanwhile, a range of different modes of procedure have become established for secondary applications during 3D imaging and image processing. Suitable operating elements, for example a computer mouse or other control media, are provided for these modes of procedures in a computed tomography machine. A workstation for imaging and image processing of computed tomograms is appropriately equipped with software in the form of a computer program product and an operator interface on a screen having appropriate operating elements with assigned functions.

In computed tomography (CT), two-dimensional tomograms of the transverse plane of a body to be examined are generally firstly made available as direct recording plane within the scope of a primary application. The transverse plane of a body is arranged here substantially perpendicular to the longitudinal axis of the body. Two-dimensional tomograms in a plane at a varied angle by comparison with the transverse plane, and/or ones that are calculated with the aid of a slab thickness different from the original slab thickness, particular a wider slab thickness, are generally denoted as multiplanar reformations (MPRs).

A possibility essential for diagnosis resides in the interactive inspection and evaluation of the image volume, mostly in a way controlled by an appropriate operating element. In a way similar to guiding a sound head in ultrasonic technology, the examiner can use such operating elements to feel his way to recognize the structures and pathological details. By moving forward and backward, the examiner can select that image in which an interesting detail is presented in the most explicit way, that is to say is displayed with the highest contrast and the greatest diameter, for example.

An extended form of the two-dimensional display resides in composing arbitrarily thick slabs from thin slabs. The term sliding thin slab (STS) has become established for this. All 2D displays have the advantage that the computed-tomography values are displayed directly and without corruption. Any possible interpolations or formations of mean values over a number of slabs can be neglected in this case. Consequently, there is always a simple orientation in the evaluation volume, which is also denoted as the volume of interest (VOI), and in the assigned 3D data volume, and the image values can always be interpreted uniquely. However, this type of monitor findings involves a large number of operations and is time consuming.

By contrast, the evaluation volume can be presented as realistically as possible by a three dimensional display of the evaluation volume. As a rule, 3D imaging and image processing is certainly the precondition for working out diagnostically relevant details in a targeted fashion. As a rule, however, the latter findings have been presented so far in a 2D display.

In the case of 3D imaging and image processing, a 3D data volume is generally made available as a basis for displaying the evaluation volume. The examiner preferably prescribes a viewer position from which he intends to view the evaluation volume. In particular, a search beam is generally made available to the examiner.

A two-dimensional image that is perpendicular to the search beam and is intended to convey a three-dimensional impression is calculated in the example. In order to build up such a display pixel by pixel (also: voxel—Acronym for "volume element") in the imaging plane, it is necessary to take account for each beam from the viewer to the respective pixel of all the CT values along the search beam through the 3D data volume, and to evaluate them. The examiner generally prescribes a pixel value, for example a contrast value, that he selects suitably for displaying a pixel. This process is necessarily repeated in the method, and so on the basis of the prescribed pixel values the examiner is shown in the context of a CT value profile for the search beam a collection of pixels that corresponds to said search beam, that is to say a 3D display of the body region/evaluation volume of interest (VOI).

Thus, within the scope of a secondary application all 3D displays can be built up either as a central projection or as a parallel projection.

A maximum intensity projection (MIP) or, in general, volume rendering (VR) is particularly suitable for a parallel projection. In the case of an MIP, the pixel with the highest CT value is determined in the projection direction along the search beam. In this case, the pixel value therefore corresponds to the maximum CT value on the search beam.

In the case of VR, it is not only that a single pixel is selected for each individual search beam emanating from the viewer's eye, but all CT values along the search beam and having a suitable weighting can supply a pixel as a contribution to the result image. Opacity and color are assigned to each pixel value via freely selectable and interactively variable transfer functions. Thus, as a result, normal soft part tissue can be selected as largely transparent, contrasted vessels as slightly opaque, and bone as strongly opaque.

Central projections that are to be preferred can be achieved, for example, by way of a surface shaded display (SSD) or of a perspective volume rendering (pVR) (or else "virtual endoscopy"). Consequently, there is the SSD or else the pSSD used in virtual endoscopy. SSD is a threshold-based surface display in the case of which a pixel is prescribed by prescribing a pixel value in the form of a threshold. For each search beam through the existing 3D data volume, that pixel is determined at which the prescribed pixel value in the form of a threshold value is reached, or exceeded for the first time as seen from the viewer.

One difference in principle between SSD and VR is that for SSD only a threshold is defined, but the surface is displayed in an opaque fashion. By contrast, in the case of the VR a number of threshold ranges are defined and are allocated covers and transparencies. Virtual endoscopy is intended to enable a perspective view of the close surroundings of the virtual "endoscopy head". Otherwise than with the actual endoscope, structures can be moved and viewed from different directions. So called fly-throughs intended to give the impression of a virtual flight through the VOI are possible. This is not only aesthetic and instructive, it can also be diagnostically valuable. In particular, a so called vessel view method serves the purpose of recording an interior of a vessel as evaluation volume.

All three-dimensional secondary applications named above process only static images.

Nevertheless, in modern medical imaging methods such as, for example, computed tomography (CT) or nuclear spin tomography or magnetic resonance tomography (MR), it is usual to scan a three-dimensional volume with a short temporal resolution. An example of a known examination is cardiac spiral CT in the case of which an admittedly limited three-dimensional volume is measured by simultaneously scanning on a number of rows of a tomogram. The data from a number of heart beats are then used from the same temporal cardiac phases within a spiral, in order to cover the entire heart volume. It is possible here, if appropriate, to trigger the data acquisition and/or data display by virtue of the fact that the primary application is coupled to an ECG unit in order to trigger identical temporal cardiac phases.

Similarly, a medical imaging method with breath triggering is known from DE 101 37 170. In this case, a navigation system is provided in order to reproduce on a scale the position of a body part moved by breathing, the recording of an image being triggered at prescribed positions.

However, such methods serve, in turn, merely for the statical display of a 3D data volume obtained. The triggering ensures in practice that images of identical phases of a periodic movement, for example of a heart or a lung, are obtained.

To the extent that data from a number of slabs are obtained at an instant, as in the case of multi-slab CT or multi-slab MRT, for example, the raw data certainly also additionally include a temporal component. Thus, a spatial-temporal 4D data record is recorded. However, there is no spatial-temporal imaging and image processing within the scope of a secondary application. Previously known three-dimensional secondary applications that aim at the perspective three-dimensional evaluations, that is to say pVR, vessel-view or fly-through methods are, in particular, not suitable for displaying a 4D data record as a multiplicity of temporally graded data volumes at a multiplicity of instants.

A type of 4D imaging in the context of ultrasonic imaging, in the case of which the movements are displayed as a rapid sequence of 3D images, is known only in its early stages. However, here it is precisely not a question of a perspective volumetric display in the abovementioned sense, but only of recording a view in the course of parallel projection. Precisely by comparison with ultrasonic systems, temporal/spatial 4D imaging and image processing in the form of a perspective volumetric display, particularly of an evaluation volume in the form of an interior of a vessel, requires computer power exceeding any previously customary. This is the case, in particular, for rapid movements at high frequency, for example of the heart, and is also relevant to data acquisition and data capacity.

Thus, a data volume of 1 Gbyte occurs in this case in only 20 seconds merely for a single complete three-dimensional imaging of the heart with a spatial resolution of 0.5 mm. Current data acquisition rates are at 200 to 300 Mbyte per recording second. In particular, possibilities of spatial-temporal 4D imaging and image processing in the form of a perspective volumetric display have so far remained completely out of consideration, since to date classic methods of endoscopy either restrict the movement of an evaluation volume through the introduction of the endoscope (for example when drawing breath), or internal views have been entirely impossible (such as in the case of the cardiac catheter).

However, in accordance with requirements of modern medical diagnostics, there would be a desire precisely for spatial-temporal imaging and image processing in the form of a perspective volumetric display.

It is an object of an embodiment of the invention to specify a method and/or an apparatus for medical imaging and/or image processing, in one example in the form of a perspective volumetric display. In one embodiment, it is possible to implement simultaneously spatial and temporal imaging and image processing, that is to say imaging and imaging processing of a 4D data volume.

With regard to the method, an object may be achieved by a method for medical imaging and image processing in the form of a perspective volumetric display, including:

providing a multiplicity of temporally graded 3D data volumes at a multiplicity of instants, a 3D data volume, respectively being assigned to an instant, prescribing a spatially absolutely fixed viewer position within an evaluation volume for at least one 3D data volume at a first instant, determining a temporal correlation between the spatially absolutely fixed viewer position and the evaluation volume for at least one further 3D data volume at at least one second instant), determining a viewer position, spatially relatively fixed in relation to the evaluation volume, within the evaluation volume for the at least one further 3D data volume at the at least one second instant, displaying the interior of the evaluation volume from a perspective of the spatially relatively fixed viewer position for the at least one further 3D data volume at the at least one second instant.

It may be possible, in principle, to provide a multiplicity of temporally graded 3D data volumes at a multiplicity of instants, for example in the form of a temporal sequence of 3D data volumes, for the purpose of a perspective volumetric display of an interior view of an evaluation volume. However, this would not normally lead to functioning spatial-temporal imaging and image processing in the form of a perspective volumetric display.

Specifically, it is normally the case that, as opposed to recording views in the course of parallel projection, it is precisely in the case of pVR methods that a moving body part chiefly varies in absolute spatial position as an example due to the movement, that is to say is subjected to a translation, in particular. Precisely for the perspective volumetric displays coming into consideration here, that is to say particularly pVR and here, in particular, virtual endoscopy, the fly-through method and the vessel view method, the display of an evaluation volume is performed from a perspective in the interior of the evaluation volume.

Conventional methods which, after all, so far do not provide 4D imaging in the form of a perspective volumetric display, would therefore necessarily need to proceed from a spatially absolutely fixed viewer position within the evaluation volume for all 3D data volumes. Only a spatially absolutely fixed viewer position is provided for all times in the case of recorded views.

In the case of the recorded views, in particular of recorded external views, a spatially absolutely fixed viewer position would not even be useful—after all, a viewer would perceive a movement of an evaluation volume in the external view, since he is seeing the evaluation volume in the view. The problem present here in perspective volumetric recordings, in particular recorded internal views, does not arise at all in the case of methods for recording views.

However, precisely in the case of the perspective methods of volumetric display addressed here, it is the goal of a diagnosis to display, in particular, the near zone of a viewers position, for example the close surroundings on a virtual "endoscope head". Furthermore, precisely in the case of the perspective volumetric displays the interior of an evaluation volume frequently involves dimensions that are smaller by a multiple than in a measure of a change in position/translation of the evaluation volume as such relative to a spatially absolutely fixed viewer position. At least one embodiment of the invention thus proceeds from the finding that previous approaches to conventional 4D imaging and image processing not only are defective but would fail, particularly where the goal is to obtain a perspective volumetric display.

By contrast, at least one embodiment of the invention provides that measures normally to be undertaken as interaction be undertaken automatically for the purpose of determining the viewer position anew and navigating through an evaluation volume. A viewer position is automatically checked by a moving evaluation volume and corrected if required.

A temporal correlation is thereby determined between the spatially absolutely fixed viewer position and the evaluation volume for at least one further 3D data volume at at least one second instant. Here correlation can be established however, in the form of an absolute relative movement of the evaluation volume in relation to the fixed viewer position.

Here, a movement of the evaluation volume can be a movement of a centroid of the evaluation volume for example. In this case, it would firstly be necessary to determine or establish the centroid of the evaluation volume. Moreover, any other possibility of establishing a movement of the evaluation volume is suitable. For example, it is also possible within the scope of the method to establish whether the spatially absolutely fixed viewer position remains within the boundaries of the evaluation volume upon transition to an evaluation volume for at least one further 3D data volume at at least one second instant.

Thus, in principle for the purpose of establishing a temporal correlation, it is sufficient to establish an arbitrary relative movement of a pixel of the evaluation volume that is of specific interest and possibly associated with a special goal, in relation to the spatially absolutely fixed viewer position. Such a temporal correlation can be determined for at least one further 3D data volume at at least one second instant.

Such a temporal correlation can also be performed by using a suitably selected number of 3D data volumes at a multiplicity of second instants. In accordance with the concept proposed here, the result of this determination is preferably present as knowledge of a relative movement of the evaluation volume in relation to the spatially absolutely fixed viewer position in a form that is more or less sufficiently quantified, depending on expediency.

Following on from the above, in accordance with the concept proposed here, the spatially absolutely fixed viewer position initially occupied is not necessarily adopted as final viewer position. It is merely used as provisional viewer position, in particular for determining the temporal correlation.

Following on from this, a spatially relatively fixed viewer position in relation to the evaluation volume is determined for the at least one further 3D data volume at the at least one second instant.

In particular, in a development the spatially relatively fixed viewer position can preserve with reference to a position mentioned above that is decisive for the translation of the evaluation volume a distance that is constant for the first instant and the at least one second instant, for example, or lies in an acceptable range. The decisive position is, for example, a centroid position or a pixel of interest, or a boundary of the evaluation volume. The distance is preferably constant for the entire multiplicity of instants, or in an acceptable range. An acceptable range will result, for example, when a deviation from a constant distance is not more than a fraction of a diameter of an evaluation volume, for example, less than 20%, and the viewer position at the same time always remains within the evaluation volume.

The concept presented here of a novel method for imaging and image processing in the form of a perspective volumetric display thus provides in one development that a spatially relatively fixed coordinate system is determined virtually for each instant in the form of a spatially absolutely fixed viewer position with reference to the evaluation volume.

The evaluation volume is displayed on this basis from a perspective of the spatially relatively fixed viewer position for the at least one further 3D data volume at the at least one second instant. Specifically, the abovementioned method steps render it possible for the first time to display the evaluation volume from a perspective within the evaluation volume, that is to say from a perspective of the spatially relatively fixed viewer position. In the case of this type of display of the evaluation volume, it is advantageously ensured in accordance with the novel concept that a viewer position for the volume segment, in the process of being viewed perspectively, of an evaluation volume is relatively at rest.

Further advantageous developments of the invention are to be gathered from the disclosed embodiments and specify in detail advantageous possibilities of implementing the method for imaging an image processing in the form of a perspective volumetric display.

As already explained in the course of the above development, it is provided, in particular, to determine a multiplicity of spatially relatively fixed viewer positions for the multiplicity of temporally graded 3D data volumes at the multiplicity of instants, and to display the evaluation volume in each case from a perspective of a spatially relatively fixed viewer position. Thus, a suitable, spatially relatively fixed viewer position is determined for the perspective volumetric display in the interior of the evaluation volume virtually for each of the multiplicity of instants.

It is possible, for example, with the aid of such a measure to use a fly-through method to "fly" through the vessels and the ventricles in a cardiac volume data record that is repeated cyclically over time and represents the beating heart. Thus, for example, the inner view of a corona artery in which the examination is being conducted can be shown, although the artery is quite definitely moved by the heart beat, because the concept presented here ensures that the spatially relatively fixed viewer position is always located inside the artery in its relative position.

This example shows that it is not absolutely necessary in each development of embodiments of the invention to preserve a constant distance of the spatially relatively fixed viewer position from a decisive position of the evaluation volume. This would admittedly be preferable, because it was then specifically be possible in this way in a particularly advantageous imaging to display only a contraction and expansion of the evaluation volume, for example, the movement of the evaluation volume being entirely free of an absolutely translational movement of the evaluation volume as such.

Nevertheless, even in the case of such a development a distance of a spatially relatively fixed viewer position from a decisive position of the evaluation volume can be varied. However, in each instance the novel concept presented here ensures that the spatially relatively fixed viewer position remains within the evaluation volume. It follows in this sense that the viewer position is spatially relatively fixed in relation to the evaluation volume. This ensures for each of the multiplicity of instants a suitable perspective volumetric display in the interior of the evaluation volume.

The imaging is preferably performed as a two-dimensional image from the perspective of a spatially relatively fixed viewer position and with a prescribed search beam.

In particular, further measures for producing a 3D effect are taken in the case of a perspective volumetric display.

Imaging in the form of two or more two-dimensional images by using two or more relatively fixed viewer positions comparatively slightly displaced from one another in space has proved to be particularly expedient. It is preferable here that each of the relatively fixed viewer positions comparatively slightly displaced from one another is assigned a search beam. In particular, the search beams cross one another, preferably at an expediently selected distance. The two or more images can be fed separately to a left and right eye of a viewer and result in a direct and clear perspective volumetric display with an effective 3D effect.

In a particularly preferred development of an embodiment of the invention, spatial-temporal (4D) imaging takes place in the form of virtual endoscopy. With the aid of the concept presented here, it is possible for the first time to examine the interior of an evaluation volume moving temporally in a more or less strongly translational fashion by using the methods of perspective volumetric display, that is to say particular with the aid of virtual endoscopy, the fly-through method or the vessel view method, without the viewer position escaping from the interior of the evaluation volume owing to the spatial/translational movement of the evaluation volume. Moreover, the concept presented here enables a multiplicity of possibilities of 4D imaging and image processing that are preferably performed as a two-dimensional image from the perspective of a particularly spatially relatively fixed viewer position and with a prescribed search beam.

It is possible here for a moving image that can be influenced in many regards to be processed and displayed sequentially or interactively.

In a development, it is possible that imaging is performed for the multiplicity of spatially relatively fixed viewer positions and at a selected instant such that the two-dimensional image is present as a spatially variable moving image. A fly-through of the evaluation volume can thus be undertaken for a fixed, selected instant.

Particularly in the context of user interaction, there is advantageously provided here the possibility of spatial navigation within a 3D data volume for a selected instant. This relates, in particular, to a possibility of spatial navigation within the evaluation volume. The user is thus able at a fixed, selective instant to use mouse or joystick, for example, to browse through views of a spatial sequence image per image, or to jump between selected views as he desires.

The concept presented here now permits influence to be exerted in an entirely similar way within the spatial-temporal 4D imaging along the time axis. It is provided, in particular, that imaging is performed for the multiplicity of instants and a selected, in particular spatially relatively fixed, viewer position such that the two-dimensional image is present as a temporally variable moving image. In the case of this type of development, it can be achieved with particular advantage that a spatially absolute translational movement of the evaluation volume is completely eliminated such that only a relative movement of the evaluation volume in relation to this spatially relatively fixed viewer position is to be seen and can be diagnosed. This applies to every type of contraction, expansion of any other relative movement within the evaluation volume, or of the evaluation volume itself.

It is preferably provided for diagnostic purposes that there is a variably settable speed for the sequence of the temporally variable moving image. In particular, there is made available to the user a possibility of temporal navigation within a 3D data volume for a selected, in particular spatially relatively fixed, viewer position. It is particularly advantageous to make available to the user a possibility of temporal navigation within the evaluation volume. The possibility of temporal navigation is to be understood as a possibility for the user to navigate or exert influence along the time axis. He can use mouse or joystick to browse views of a temporal sequence image by image, or to jump between selected views as he desires.

It is possible in the context of a development, for example, to decelerate or accelerate the time by comparison with real time, in order, for example, to be able to assess more effectively rapid heart movements or slow colon movements. A user can also move forward and backward on the time axis in steps or continuously.

The concept proposed here has a high potential in the context of the pVR within the scope of future applications. In particular, the concept proposed here proves to be advantageous in an imaging method where 3D imaging is performed as virtual endoscopy. Such virtual endoscopic views, which are also to be noted as endoluminal views, are virtually a perspective VR.

The leading field of use of this technique is anatomical structures that are also accessable to endoscopes. They include, for example, the bronchial tree, relatively large vessels, the colon and the paranasal sinus system. Moreover, they can also be used in regions such as renal cisterns and in the gastrointestinal region, which are not directly accessable to endoscopes.

However, spatial-temporal imaging and image processing in the form of a perspective volumetric display according to the concept described above proved to be particularly suitable precisely for applications such as have not so far been accessible to the classic endoscopes. This relates, in particular, to observations of the blood circulation such as corona arteries, main arteries, veins and there, in particular, the display of a vein pump. Moreover, entirely new fields of use open up in the region of the ventricles and the cardiac valves under the influence of the blood circulation. Likewise, it is possible to use the concept proposed here to examine the influence of breathing on the bronchia. The novel concept proves to be particularly advantageous precisely for regions relating to moving evaluation volumes that have so far not been accessible to endoscopes.

In particular, the method proves to be advantageous in imaging methods that proceed from a 3D data volume obtained by using a contrast agent. This relates in particular to the blood circulation, that is to say blood vessels and the heart, coloscopy, bronchioscopy and, if appropriate, also cisternoscopy. Computed tomograms of a colon or a bronchia or a cistern are imaged and subjected to image processing for this purpose within the scope of the embodiments of the method explained. It should nevertheless be clear that the concept explained and claimed here is likewise useful for imaging and image processing in the context of medical imaging in the case of which the data volume was obtained in the context of other procedures.

The 2D or 3D data volume can also be obtained, for example, in the context of magnetic resonance tomography (MRT). Specifically, it has emerged that there is also frequently a need in MRT to examine moving evaluation volumes, in which case it can be advantageous in accordance with the proposed concept to correct the viewer position as a relatively fixed viewer position. One example would be an examination of moving blood, marked with the aid of a contrast agent, inside a vessel. This would lead to a spatial displacement of the signal, which would be compensated in accordance with the proposed concept by correcting the viewer position. The proposed concept proves to be especially advantageous when applied to MRT, as the temporal resolution of the MRT is increasingly better.

Another field of application would be positron emission tomography (PET)

With regard to the apparatus, an object may be achieved by at least one embodiment of the invention by way of a computer-tomography machine that has at least one operating element for carrying out the method. Such an apparatus could be implemented, for example, in the form of a so called gantry tube with associated operating elements.

Another example would be an apparatus in the field of digital radiography, in particular a so called C-arc radiography apparatus, which is generally an open apparatus. In particular, in this design the x-ray source and detector are respectively fitted at the end of a C-shaped arc. The term C-arc computed tomography has become established in this context.

With regards to the apparatus, at least one embodiment of the invention also leads to a workstation for imaging and image processing of computed tomograms that has at least one operating element for carrying out the method explained above.

An operating element is to be understood, in particular, as a software device, for example a software module, a device driver, and/or a hardware device, for example a joystick, a mouse or the surface of a display screen, individually or in combination, with the aid of which operating element it is possible to execute and control one of the abovementioned method steps of at least one embodiment.

At least one embodiment of the invention also leads to a computer program product for imaging and image processing of computed tomograms that has at least one program module for carrying out the method of at least one embodiment explained above.

In particular, it is possible to build up a computer program product on the basis of previously known program products relating to three-dimensional perspective secondary applications such as the fly-through method, virtual endoscopy or the vessel view method in such a way that a spatial-temporal 4D data volume is processed as input, and calculations can be carried out on the basis thereof. In particular, a computer program product has, furthermore, a program module for determining a viewer position that is spatially relatively fixed in relation to the evaluation volume for the at least one further 3D data volume at the at least one second instant.

BRIEF DESCRIPTION OF THE DRAWINGS

Example embodiments of the invention are described below with the aid of the drawings in which, in detail:

FIG. 2 shows a flowchart of a particularly preferred embodiment of the method in accordance with the proposed concept.

DETAILED DESCRIPTION OF THE EXAMPLE EMBODIMENTS

Figure 1:
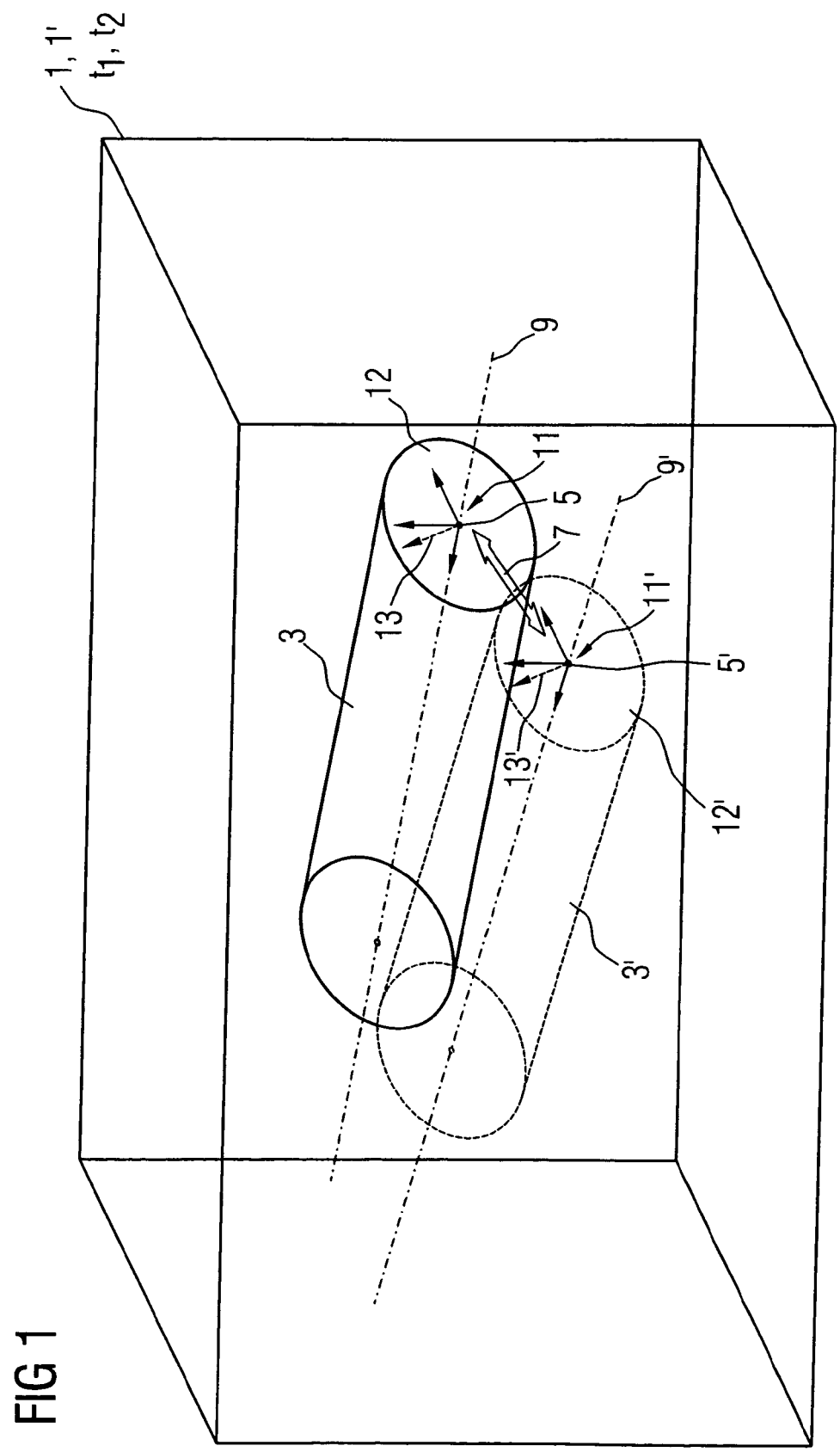
FIG. 1 shows an example application of the proposed concept in the context of a particularly preferred embodiment, the spatially absolutely fixed viewer position being provided within an evaluation volume for a 3D data volume at a first instant, and a temporal correlation being determined between the spatially absolutely fixed viewer position and the evaluation volume for a further 3D data volume at the second instant.

FIG. 1 illustrates an example application of the method according to the proposed concept. A preferred example embodiment of the method is explained by the example of a 3D data volume 1, 1' in the form of a cardiac volume data record. For the sake of simplicity, in the case of the example explained in FIG. 1 the extent of a 3D data volume 1 at a first instant $t_1$ is shown in a fashion corresponding to the extent of a 3D data volume 1' at an instant $t_2$, for which reason both 3D data volumes 1, 1' are represented by the same box.

In the present example, the problem arises that the position of an evaluation volume 3 in the form of a vessel is varied, and so also in its absolute spatial position, by the heart beat, and said evaluation volume is therefore subject to a translational movement. Whereas the vessel is to be found as evaluation volume 3 in the 3D data volume 1 at the instant $t_1$, at an instant $t_2$ it occupies in the 3D data volume 1' a different position, which is illustrated by dashes in FIG. 1, specifically the position of the evaluation volume 3' in the 3D data volume 1' at the instant $t_2$. The evaluation volume 3 as well as the evaluation volume 3' designate the same vessel in the present case.

The present method prescribes a spatially absolutely fixed viewer position 5 within the evaluation volume 3 for the 3D data volume 1 at the first instant $t_1$. Were the spatially absolutely fixed viewer position 5 to be retained in the course of conventional methods, at an instant $t_2$ the same spatially absolutely fixed viewer position 5 would be situated outside the evaluation volume 3', and thus outside the vessel. A perspective volumetric display within the evaluation volume 3' would therefore already no longer be possible at the instant $t_2$.

Consequently, within the scope of the particularly preferred embodiments illustrated here the method provides an determination of a temporal correlation 7 between the spatially absolutely fixed viewer position 5, on the one hand, and the evaluation volume 3' for the further 3D data volume 1' at the second instant $t_2$, on the other hand. In order to determine the temporal correlation between the spatially absolutely fixed viewer position 5 and the evaluation volume 3', use is made of at least one interrogation that establishes whether the spatially absolutely fixed viewer position 5 at the instant $t_2$ is still located within the evaluation volume 3'. Owing to the heart beat, the latter has changed its position by comparison with the instant $t_1$ only at the instant $t_2$.

In the embodiment illustrated in FIG. 1, a decisive position of the evaluation volume 3, 3' is determined by determining a centroid 9 for the evaluation volume 3, and a centroid 9' for the evaluation volume 3'. The sequence of centroids 9, 9' is illustrated in FIG. 1 by a dashed and dotted line. Thus, the centroid movement of the evaluation volume 3 by comparison with the evaluation volume 3' is to be established from comparing the instants $t_1$ and $t_2$.

The temporal correlation 7 is determined by establishing at the instant $t_1$ a distance of the spatially absolutely fixed viewer position 5 from the centroid 9. The distance of the spatially absolutely fixed viewer position 5 from the centroid 9' is established at the instant $t_2$. Thus, as a result, different distances are established at the instant $t_1$ and the instant $t_2$, and this constitutes the temporal correlation.

On the basis of this result, a viewer position 5' that is spatially relatively fixed in relation to the evaluation volume 3' is determined for the further 3D data volume 1' at the second instant $t_2$. This can be performed in principle in any arbitrarily expedient way depending on the application. In the present example of FIG. 1, the spatially relatively fixed viewer position 5' is selected in the form of a centroid 9'.

The determination of the centroid 9, 9' can be executed in manifold ways. The details of the medical application and of the geometric structure of the evaluation volume 3, 3' are to be taken into account in the process. In particular, it is also possible to perform a weighted centroid determination that operates with suitable weighting with reference to the evaluation volume 3, 3'. In the present example, this spatially absolutely fixed viewer position 5 and the spatially relatively fixed viewer position 5' are selected for the sake of simplicity as the center of the opening surface 12, 12' of the evaluation volume 3, 3' in the form of a vessel.

The viewer position 5, 5' is selected by way of example in the form of a coordinate system 11, 11', which is moved along with the evaluation volume 3, 3' illustrated, is spatially relatively fixed in relation to the evaluation volume 3, 3' and is selected in the present example as a centroid coordinate system 11, 11' that is moved along with the evaluation volume 3, 3'.

The imaging in the interior of the evaluation volume 3, 3' is performed from the perspective of the spatially relatively fixed viewer position 5' and the provisional spatially absolutely fixed viewer position 5, and in each case with a prescribed search beam 13, 13' in the coordinate system 11, 11' moving along therewith. This particularly permits the perspective display of the near field around the viewer position 5, 5'. Such a pVR is similar to a display that would have been obtained with the aid of an endoscope head arranged at the viewer position 5, 5'.

The method has been explained with the aid of FIG. 1 only by way of example for a first instant $t_1$ and a second instant $t_2$. In practice, the design of the method can certainly be restricted to two instants, or to a number of suitably selected instants.

In the present example, the method in accordance with the novel concept implies a determination of a multiplicity (not illustrated in more detail) of spatially relatively fixed viewer positions similar to the viewer position 5'.

The method is thus carried out with particular advantage in the way explained here for a multiplicity of instants $t_i$, i=1, 2, 3, . . . (not illustrated). In this case, a multiplicity of spatially relatively fixed viewer positions are determined, in a way similar to the viewer position 5', for the multiplicity of temporally graded 3D data volumes, similar to the data volume 1', at the multiplicity of instants $t_i$, and in each case an evaluation volume similar to the evaluation volume 3' is displayed from a perspective of a spatially relatively fixed viewer position similar to the viewer position 5'. In the example illustrated, this advantageously leads to a spatial-temporal 4D display of a vessel to be diagnosed in the form of a virtual endoscopy. The imaging is performed as a two-dimensional image with a spatially perspective effect.

Going beyond the present example, it is possible for virtually every absolutely spatial translational movement of the evaluation volume 3, 3'—in the form of a vessel, here—to be eliminated from the 4D imaging on the basis of the determined temporal correlation 7 between the instants $t_1, t_2, \ldots t_i$, i=1, 2, 3 . . . . Consequently, it is possible from the view of a spatially relatively fixed viewer position 5, 5', that is to say within the framework of a coordinate system 11, 11' that is moving along but is fixed in relation to the evaluation volume 3, 3', for each actual variation in the vessel illustrated in FIG. 1—for example a contraction or an expansion or other interesting processes inside the vessel—to be authentically displayed.

A multiplicity of valuable diagnostic possibilities result from the display of the vessel without disturbing translational effects. In particular, imaging can be performed for the multiplicity of instants $t_i$, i=1, 2, 3, . . . , and for a selected spatially relatively fixed viewer position 5, 5' such that two-dimensional image is present as a temporally variable moving image. This moving image can run at a variably settable speed, or the user can browse the moving image page by page, that is to say time step by time step $t_i$.

Thus, in the case of the embodiment of the method illustrated here, a suitable viewer position 5, 5', in particular a suitable spatially relatively fixed viewer position 5', is determined at each instant $t_1, t_2, \ldots t_i$, i=1, 2, 3 . . . for a perspective display of the vessel from a coordinate system 11, 11' that is moving along, and with the use of an appropriate search beam 13, 13'. The viewer position 5, 5' is relatively at rest for the volume segment of the evaluation volume 3, 3' which is being viewed perspectively. The present embodiment in this way permits the internal view of a coronary artery in which the examination is being conducted, although the artery is moving in absolute terms owing to the heart beat, because the viewer position 5, 5' is situated inside the artery.

FIG. 2 shows a flowchart of a particularly preferred embodiment of the method of computed tomography, starting from a 3D data volume obtained using a contrast agent. After the start 21 of the method, a multiplicity of temporally graded 3D data volumes $V_1, V_2, V_3, \ldots V_i$ are provided in method step 23 at a multiplicity of instants $t_1, t_2, t_3, \ldots t_i$, a 3D data volume $V_i$ being assigned in each case to an instant $t_i$. Here, the index i stands for natural numbers 1, 2, 3 etc., if appropriate up to a maximum number n, and enumerates the 3D data volumes $V_i$ and numbers the 3D data volumes $V_i$ and the instants consecutively.

A spatially absolutely fixed viewer position $O_1$ within an evaluation volume is prescribed in method step 25 for at least one 3D data volume $V_1$ at a first instant $t_1$. The viewer position $O_1$ can be selected, for example, in the form of a viewer position 5 of FIG. 1. The evaluation volume can be selected, for example, in the form of an evaluation volume 3 of FIG. 1.

A temporal correlation is determined in step 27 between the spatially absolutely fixed viewer position $O_1$ and the evaluation volume for at least one further 3D data volume $V_2$ at at least one second instant $t_2$. The correlations are illustrated in method step 27 by way of example between a viewer position $O_1$ and a 3D data volume $V_3$, and between a viewer position $O_1$ and a 3D data volume $V_i$, i=1, 2, 3 . . . .

A viewer position $O_2$, $O_3$ that is spatially relatively fixed in relation to the evaluation volume is determined in method step 29 for second instants $t_2$, $t_3$, . . . $V_i$. The spatially relatively fixed viewer position $O_i$ can be selected, for example, in the form of a spatially relatively fixed viewer position 5', illustrated in FIG. 1, for the evaluation volume 3'.

The evaluation volume is displayed in method step 31 from a perspective of the viewer position $O_1$, $O_2$, $O_3$ . . . $O_i$ for the 3D data volumes $V_1$, $V_2$, $V_3$, . . . $v_i$ at the instants $t_1$, $t_2$, $t_3$, . . . $t_i$, i=1, 2, 3 . . .

Up to the end 35, the method can be supplemented by a multiplicity of possibilities of display and inter-action for the two-dimensional temporally variable moving image, for example by interaction of the user in method step 33, during which it is possible to set a sequence of the temporally variable moving image with a variable speed, or the moving image can be browsed page by page.

The method steps 21 and 35 illustrated in FIG. 2 can also constitute an operating element for carrying out the method in the case of a computed tomography machine or a workstation for imaging and image processing of computed tomograms. In particular, the method steps 21 and 35 illustrated in FIG. 2 can constitute a program module for carrying out the method in the case of a computer program product for imaging and image processing of computed tomograms.

In particular, method step 29 can be interpreted as a program module in the case of a computer program product, the program module determining a viewer position $O_2$, $O_3$ . . . $O_i$, which is spatially relatively fixed in relation to the evaluation volume, for the at least one further 3D data volume $V_2$, $V_3$ . . . $V_i$ at the at least one second instant $t_2$, $t_3$ . . . $t_i$.

In order to enable advantageous spatial/temporal imaging and image processing in the form of a perspective volumetric display, a method of at least one embodiment provides the following steps in the context of the novel concept:

a method for medical imaging and image processing in the form of a perspective volumetric display, having the method steps of:

providing a multiplicity of temporally graded 3D data volumes 1, 1', V at a multiplicity of instants $t_1$, $t_2$, $t_i$, a 3D data volume 1, 1', $V_i$, respectively being assigned to an instant $t_1$, $t_2$, $t_i$, prescribing a spatially absolutely fixed viewer position 5, $O_i$ within an evaluation volume 3 for at least one 3D data volume 1, $V_1$ at a first instant $t_i$, determining a temporal correlation 7 between the spatially absolutely fixed viewer position 5, $O_1$ and the evaluation volume 3' for at least one further 3D data volume 1', $V_i$ at at least one second instant $t_2$, $t_i$, determining a viewer position 5', $O_i$, spatially relatively fixed in relation to the evaluation volume 3', for the at least one further 3D data volume 1', $V_i$ at the at least one second instant $t_2$, $t_i$, displaying the evaluation volume 3' from a perspective of the spatially relatively fixed viewer position 5', $O_i$ for the at least one further 3D data volume 1', $V_i$ at the at least one second instant $t_2$, $t_i$, Any of the aforementioned methods may be embodied in the form of a system or device, including, but not limited to, any of the structure for performing the methodology illustrated in the drawings.

Further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, such as floppy disks (trademark), cassette tapes, and removable hard disks; media with a built-in rewriteable non-volatile memory, such as memory cards; and media with a built-in ROM, such as ROM cassettes.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for medical imaging and image processing in the form of a perspective volumetric display, the method comprising:

providing a multiplicity of temporally graded 3D data volumes at a multiplicity of instants ($t_1$, $t_2$, $t_i$), a 3D data volume, respectively being assigned to an instant;

prescribing a spatially absolutely fixed first viewer position within an evaluation volume for at least one 3D data volume at a first instant, said evaluation volume is a moving body part which varies its absolute spatial position in time;

determining a temporal correlation between the spatially absolutely fixed first viewer position and the evaluation volume for at least one further 3D data volume at at least one second instant;

determining a second viewer position, spatially relatively fixed in relation to the evaluation volume, within the evaluation volume for the at least one further 3D data volume at the at least one second instant; and displaying the interior of the evaluation volume from a perspective of the spatially relatively fixed second viewer position for the at least one further 3D data volume at the at least one second instant.

2. The method as claimed in claim 1, further comprising: determining a multiplicity of spatially relatively fixed viewer positions for the multiplicity of temporally graded 3D data volumes at the multiplicity of instants, and displaying the evaluation volume in each case from a perspective of a spatially relatively fixed viewer position.

3. The method as claimed in claim 1, wherein the displaying further displays a two-dimensional image from the perspective of a spatially relatively fixed viewer position and with a prescribed search beam.

4. The method as claimed in claim 1, wherein the displaying further displays two or more two-dimensional images by using two or more relatively fixed viewer positions comparatively slightly displaced from one another in space.

5. The method as claimed in claim 4, wherein each of the relatively fixed viewer positions comparatively slightly displaced from one another is assigned a search beam.

6. The method as claimed in claim 1, wherein the displaying displays views representing a virtual endoscopy.

7. The method as claimed in claim 1, wherein imaging is performed for the multiplicity of viewer positions and at a selected instant, such that the two-dimensional image is present as a spatially variable moving image.

8. The method as claimed in claim 1, wherein spatial navigation is used within a 3D data volume for a selected instant.

9. The method as claimed in claim 1, wherein imaging is performed for the multiplicity of instants and a selected viewer position such that the two-dimensional image is present as a temporally variable moving image.

10. The method as claimed in claim 9, wherein a variably settable speed is used for the sequence of the temporally variable moving image.

11. The method as claimed in claim 1, wherein temporal navigation is used within a 3D data volume for a selected viewer position.

12. The method as claimed in claim 1, wherein the method for medical imaging and image processing is an imaging method in computed tomography.

13. The method as claimed in claim 1, wherein the method for medical imaging and image processing is an imaging method in magnetic resonance tomography.

14. The method as claimed in claim 1, wherein the method is preceding from a 3D data volume obtained by using a contrast agent.

15. The method as claimed in claim 1, wherein the method is for imaging and image processing of computed tomograms inside a colon.

16. The method as claimed in claim 1, wherein the method is for imaging and image processing of computed tomograms inside a bronchus.

17. The method as claimed in claim 1, wherein the method is for imaging and image processing of computed tomograms inside a blood vessel.

18. The method as claimed in claim 1, wherein the method is for imaging and image processing of computed tomograms inside a heart.

19. A computed tomography machine comprising operating elements for performing the method of claim 1.

20. A workstation for imaging and image processing of computed tomograms comprising operating elements for performing the method of claim 1.

21. A computer program product storing executable instructions, which when executed by a computer system, causes the computer system to perform the method of claim 1.

22. The method as claimed in claim 2, wherein the displaying further displays a two-dimensional image from the perspective of a spatially relatively fixed viewer position and with a prescribed search beam.

23. The method as claimed in claim 2, wherein the displaying displays views representing a virtual endoscopy.

24. A computed tomography machine, comprising:
means for providing a multiplicity of temporally graded 3D data volumes at a multiplicity of instants ($t_1$, $t_2$, $t_i$), a 3D data volume, respectively being assigned to an instant;
means for prescribing a spatially absolutely fixed first viewer position within an evaluation volume for at least one 3D data volume at a first instant, said evaluation volume is a moving part which varies its absolute spatial position in time;
means for determining a temporal correlation between the spatially absolutely fixed first viewer position and the evaluation volume for at least one further 3D data volume at at least one second instant;
means for determining a second viewer position, spatially relatively fixed in relation to the evaluation volume, within the evaluation volume for the at least one further 3D data volume at the at least one second instant; and
means for displaying the interior of the evaluation volume from a perspective of the spatially relatively fixed second viewer position for the at least one further 3D data volume at the at least one second instant.

25. A workstation for imaging and image processing of computed tomograms, comprising:
means for providing a multiplicity of temporally graded 3D data volumes at a multiplicity of instants ($t_1$, $t_2$, $t_i$), a 3D data volume, respectively being assigned to an instant;
means for prescribing a spatially absolutely fixed first viewer position within an evaluation volume for at least one 3D data volume at a first instant said evaluation volume is a moving body part which varies its absolute spatial position in time;
means for determining a temporal correlation between the spatially absolutely fixed first viewer position and the evaluation volume for at least one further 3D data volume at at least one second instant;
means for determining a second viewer position, spatially relatively fixed in relation to the evaluation volume, within the evaluation volume for the at least one further 3D data volume at the at least one second instant; and
means for displaying the interior of the evaluation volume from a perspective of the spatially relatively fixed second viewer position for the at least one further 3D data volume at the at least one second instant.

* * * * *